United States Patent
Mahajan et al.

(10) Patent No.: US 12,295,735 B2
(45) Date of Patent: May 13, 2025

(54) SYSTEMS AND METHODS FOR DETECTING ARRHYTHMIAS

(71) Applicant: Cardiac Pacemakers, Inc., St. Paul, MN (US)

(72) Inventors: Deepa Mahajan, North Oaks, MN (US); David L. Perschbacher, Coon Rapids, MN (US); Sunipa Saha, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 371 days.

(21) Appl. No.: 16/705,654

(22) Filed: Dec. 6, 2019

(65) Prior Publication Data
US 2020/0178826 A1    Jun. 11, 2020

Related U.S. Application Data

(60) Provisional application No. 62/776,346, filed on Dec. 6, 2018.

(51) Int. Cl.
*A61B 5/00* (2006.01)
*A61B 5/024* (2006.01)
(Continued)

(52) U.S. Cl.
CPC ............ *A61B 5/361* (2021.01); *A61B 5/0031* (2013.01); *A61B 5/02405* (2013.01); *A61B 5/363* (2021.01); *A61B 5/7275* (2013.01)

(58) Field of Classification Search
CPC ....... A61B 5/361; A61B 5/363; A61B 5/0031; A61B 5/02405; A61B 5/7275; A61B 5/686
See application file for complete search history.

(56) References Cited

U.S. PATENT DOCUMENTS 5,713,367 A * 2/1998 Arnold ................. A61B 5/4884
                                                         600/517
6,959,212 B2 * 10/2005 Hsu ...................... A61N 1/3622
                                                         600/518
(Continued)

FOREIGN PATENT DOCUMENTS

WO    WO-2020118150 A1    6/2020

OTHER PUBLICATIONS

"International Application Serial No. PCT/US2019/064869, International Preliminary Report on Patentability mailed Jun. 17, 2021", 7 pgs.

(Continued)

*Primary Examiner* — Sana Sahand
(74) *Attorney, Agent, or Firm* — Schwegman Lundberg & Woessner, P.A.

(57) ABSTRACT

Systems and methods for detecting cardiac arrhythmia are discussed. An exemplary arrhythmia detection system can receive physiologic information of the patient, measure a first signal metric using a first portion of the received physiologic information, and determine an arrhythmia detection duration using a comparison between the measured first signal metric and a reference signal metric value. The system includes an arrhythmia detector to detect an AT episode using a second portion of the physiologic information corresponding to the determined arrhythmia detection duration.

20 Claims, 5 Drawing Sheets

(51) Int. Cl.
*A61B 5/361* (2021.01)
*A61B 5/363* (2021.01)

(56) References Cited

U.S. PATENT DOCUMENTS

| | | | |
|---|---|---|---|
| 8,204,592 B1 * | 6/2012 | Ostrow | G16H 40/67 |
| | | | 607/14 |
| 10,368,769 B2 | 8/2019 | Cao et al. | |
| 2008/0051843 A1 * | 2/2008 | Li | A61N 1/39622 |
| | | | 607/9 |
| 2010/0317984 A1 * | 12/2010 | McCarthy | A61B 5/361 |
| | | | 600/518 |
| 2012/0035491 A1 * | 2/2012 | Mahajan | A61N 1/3621 |
| | | | 600/518 |
| 2016/0045125 A1 | 2/2016 | Krueger et al. | |
| 2016/0287177 A1 * | 10/2016 | Huppert | A61B 5/486 |
| 2017/0281033 A1 | 10/2017 | Higgins et al. | |
| 2018/0028086 A1 | 2/2018 | Cao et al. | |
| 2018/0104502 A1 | 4/2018 | Perschbacher et al. | |
| 2018/0192902 A1 | 7/2018 | Perschbacher et al. | |
| 2018/0256059 A1 | 9/2018 | Perschbacher et al. | |

OTHER PUBLICATIONS

"International Application Serial No. PCT/US2019/064869, International Search Report mailed Apr. 3, 2020", 5 pgs.
"International Application Serial No. PCT/US2019/064869, Written Opinion mailed Apr. 3, 2020", 5 pgs.

* cited by examiner

SYSTEMS AND METHODS FOR DETECTING ARRHYTHMIAS

CLAIM OF PRIORITY

This application claims the benefit of priority under 35 U.S.C. § 119(e) of U.S. Provisional Patent Application Ser. No. 62/776,346, filed on Dec. 6, 2018, which is herein incorporated by reference in its entirety.

TECHNICAL FIELD

This document relates generally to medical devices, and more particularly, to systems, devices and methods for detecting and managing cardiac arrhythmias.

BACKGROUND

Implantable medical devices (IMDs) have been used for monitoring patient health condition or disease states and delivering therapies. For example, implantable cardioverter-defibrillators (ICDs) may be used to monitor for certain abnormal heart rhythms and to deliver electrical energy to the heart to correct the abnormal rhythms. Some IMDs may be used to monitor for chronic worsening of cardiac hemodynamic performance, such as due to congestive heart failure (CHF), and to provide cardiac stimulation therapies, including cardiac resynchronization therapy (CRT) to correct cardiac dyssynchrony within a ventricle or between ventricles.

Some IMDs can detect cardiac arrhythmias, such as atrial tachyarrhythmia. One type of atrial tachyarrhythmia is atrial fibrillation (AF), recognized as the most common clinical arrhythmia affecting millions of people. During AF, disorganized electrical pulses originated from regions in or near an atrium may lead to irregular conductions to ventricles, thereby causing inappropriately fast and irregular heart rate. AF may be paroxysmal that may last from minutes to days before it stops by itself. Persistent AF may last for over a week and typically requires medication or other treatment to revert to normal sinus rhythm. AF is permanent if a normal heart rhythm cannot be restored with treatment. AF may be associated with stroke and requires anticoagulation therapy.

Another type of atrial tachyarrhythmia is atrial flutter (AFL). AFL usually accompanies with some degree of atrioventricular (AV) node conduction block, and can be associated with a fast and usually regular heart rate. Typical or Type I AFL may involve a single reentrant circuit in the right atrium around the tricuspid valve annulus, and has an atrial rate of 240 to 340 beats per minute (bpm). The reentrant circuit most often travels in a counter-clockwise direction. Atypical or Type II AFL follows a different circuit, which may involve the right or the left atrium, and usually has a faster atrial rate of around 340-440 bpm. AFL may be associated with a variety of cardiac disorders, such as coronary artery disease (CAD) or hypertensive heart disease. AFL may often degenerate into AF. Prolonged fast AFL may lead to decompensation with loss of normal heart function. This may manifest as effort intolerance, nocturnal breathlessness, or swelling of the legs or abdomen.

Timely detection of atrial tachyarrhythmia, such as AF or AFL, may be clinically important for assessing cardiac function. Some atrial tachyarrhythmia may be characterized by slow and stable ventricular rates. Such atrial tachyarrhythmic episodes may be mistakenly recognized by an IMD as a sinus rhythm, and are undetected or under-detected in some patients. This may have adverse impact on patient outcome.

OVERVIEW

This document discusses, among other things, systems, devices, and methods for detecting cardiac arrhythmias, such as an atrial tachyarrhythmia (AT). An exemplary arrhythmia detection system includes a detection criterion circuit that can receive physiologic information of the patient, measure a first signal metric using a first portion of the received physiologic information, and determine an arrhythmia detection duration using a comparison between the measured first signal metric and a reference signal metric value. The system includes an arrhythmia detector that can detect an AT episode using a second portion of the physiologic information corresponding to the determined arrhythmia detection duration. In some examples, the arrhythmia detector can identify the AT episode as a sustained or a non-sustained episode based on whether a second signal metric in the second portion of the physiologic information consistently satisfies a detection criterion through the determined arrhythmia detection duration. In other examples, such as where identifications are made at intervals within a duration, the arrhythmia detector can identify the AT episode as a sustained or non-sustained episode based on whether a second signal metric in the second portion of the physiologic information satisfies a detection criterion through the determined arrhythmia detection duration.

Example 1 is a system for detecting cardiac arrhythmia (AT) in a patient. The system comprises a detection criterion circuit and an arrhythmia detector circuit. The detection criterion circuit can be configured to receive physiologic information of the patient; measure a first signal metric using a first portion of the received physiologic information, and compare the first signal metric to one or more thresholds, and determine an atrial tachyarrhythmia (AT) detection criterion based on the comparison. The arrhythmia detector circuit can be configured to detect an AT episode using a second portion of the physiologic information and the determined AT detection criterion.

In Example 2, the subject matter of Example 1 optionally includes the detection criterion circuit that can be configured to determine an arrhythmia detection duration using a comparison between the measured first signal metric and a reference detection threshold, and the detector circuit that can be configured to identify the AT episode as a sustained AT if the second portion of the physiologic information satisfies a detection criterion through the determined arrhythmia detection duration, determine that no AT episode is present if the second portion of the physiologic information fails to satisfy the detection criterion through the determined arrhythmia detection duration, and identify the AT episode as a non-sustained AT if the second portion of the physiologic information inconsistently satisfies the detection criterion during the determined arrhythmia detection duration.

In Example 3, the subject matter of any one or more of Examples 1-2 optionally includes the detection criterion circuit that can be configured to determine the arrhythmia detection duration to be inversely proportional to a deviation of the measured first signal metric from the reference detection threshold.

In Example 4, the subject matter of any one or more of Examples 1-3 optionally includes a detection zone circuit that can be configured to generate a plurality of detection zones each characterized by respective non-overlapping value ranges of the first signal metric with respect to the reference detection threshold. The detection criterion circuit can be configured to determine, for the plurality of detection zones, respective zone-specific arrhythmia detection durations. The arrhythmia detector circuit can be configured to: recognize, among the plurality of detection zones, a detection zone having a corresponding value range including the measured first signal metric; and detect the sustained AT episode in the recognized detection zone using the second portion of the physiologic information during the zone-specific arrhythmia detection duration (ZDur) corresponding to the recognized detection zone.

In Example 5, the subject matter of Example 4 optionally includes the zone-specific arrhythmia detection durations that can be inversely proportional to deviations of the respective value ranges of the plurality of detection zones from the reference detection threshold.

In Example 6, the subject matter of any one or more of Examples 4-5 optionally includes the plurality of detection zones that can include: a first detection zone characterized by a first value range of the first signal metric that exceeds the reference detection threshold by a first margin, the first detection zone having a first ZDur; and a second detection zone characterized by a second value range of the first signal metric that is below the reference detection threshold by a second margin, the second detection zone having a second ZDur.

In Example 7, the subject matter of Example 6 optionally includes the second ZDur is longer than the first ZDur.

In Example 8, the subject matter of any one or more of Examples 6-7 optionally includes the arrhythmia detector circuit that can be configured to identify the AT episode as a sustained AT in the first detection zone if the second portion of the physiologic information satisfies a detection criterion through the first ZDur, and determine that no AT episode is present in the second detection zone if the second portion of the physiologic information fails to satisfy the detection criterion through the second ZDur.

In Example 9, the subject matter of any one or more of Examples 6-8 optionally includes the plurality of detection zones that can further include a third detection zone characterized by a third value range that lies between the first value range and the second value range, the third detection zone having a third ZDur longer than the first ZDur and the second ZDur.

In Example 10, the subject matter of any one or more of Examples 4-9 optionally includes the arrhythmia detector circuit that can be configured to measure a second signal metric using the second portion of the received physiologic information, identify the AT episode as a sustained AT in the recognized detection zone if the measured second signal metric exceeds a zone-specific detection threshold (ZTh) through the ZDur corresponding to the recognized detection zone, and determine no AT episode is present in the recognized detection zone if the measured second signal metric is below the ZTh through the ZDur corresponding to the recognized detection zone.

In Example 11, the subject matter of Example 10 optionally includes the ZTh that can be a lower bound of the value range of the recognized detection zone.

In Example 12, the subject matter of any one or more of Examples 10-11 optionally includes the first and second signal metrics, each of which may include one of: an atrial heart rate; a ventricular heart rate variability; a ventricular rate cluster; a Wenckebach score; a double-decrement ratio; and a cardiac signal morphology.

In Example 13, the subject matter of Example 12 optionally includes the first and second signal metrics that can be the same signal type.

In Example 14, the subject matter of Example 12 optionally includes the first and second signal metrics that can be different signal metric types.

In Example 15, the subject matter of any one or more of Examples 1-14 optionally includes a therapy circuit configured to initiate or adjust a therapy in response to the detected AT episode.

Example 16 is a method for detecting cardiac arrhythmia in a patient. The method comprises steps of: receiving physiologic information of the patient; measuring a first signal metric via a detection criterion circuit using a first portion of the received physiologic information; comparing the first signal metric to one or more thresholds, and determining an atrial tachyarrhythmia (AT) detection criterion based on the comparison; and detecting an AT episode via an arrhythmia detector circuit using a second portion of the physiologic information and the determined AT detection criterion.

In Example 17, the subject matter of Example 16 optionally includes determining an arrhythmia detection duration based on a comparison between the measured first signal metric and a reference detection threshold, and the step of detecting the AT episode can include steps of: identifying the AT episode as a sustained AT if the second portion of the physiologic information satisfies a detection criterion through the determined arrhythmia detection duration; determining that no AT episode is present if the second portion of the physiologic information fails to satisfy the detection criterion through the determined arrhythmia detection duration; and identifying the AT episode as a non-sustained AT if the second portion of the physiologic information inconsistently satisfies the detection criterion during the determined arrhythmia detection duration.

In Example 18, the subject matter of any one or more of Examples 16-17 optionally includes the arrhythmia detection duration that can be inversely proportional to a deviation of the measured first signal metric from the reference detection threshold.

In Example 19, the subject matter of any one or more of Examples 16-18 optionally includes steps of: generating a plurality of detection zones each characterized by respective non-overlapping value ranges of the first signal metric with respect to the reference detection threshold; determining, for the plurality of detection zones, respective zone-specific arrhythmia detection durations; and recognizing, among the plurality of detection zones, a detection zone having a corresponding value range within including measured first signal metric. The step of detecting an AT episode can include detecting a sustained AT episode in the recognized detection zone using the second portion of the physiologic information during the zone-specific arrhythmia detection duration (ZDur) corresponding to the recognized detection zone.

In Example 20, the subject matter of Example 19 optionally includes the plurality of detection zones that can include: a first detection zone characterized by a first value range of the first signal metric that exceeds the reference detection threshold by a first margin, the first detection zone having a first ZDur; a second detection zone characterized by a second value range of the first signal metric that is below the reference detection threshold by a second margin, the second detection zone having a second ZDur; and a third detection zone characterized by a third value range that lies between the first value range and the second value range, the third detection zone having a third ZDur longer than the first ZDur and the second ZDur.

In Example 21, the subject matter of any one or more of Examples 19-20 optionally includes measuring a second signal metric using the second portion of the received physiologic information. The step of detecting a sustained AT episode an include identifying the AT episode as a sustained AT in the recognized detection zone if the measured second signal metric exceeds a zone-specific detection threshold (ZTh) through the ZDur corresponding to the recognized detection zone, and determining that no AT episode is present in the recognized detection zone if the measured second signal metric is below the ZTh through the ZDur corresponding to the recognized detection zone.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
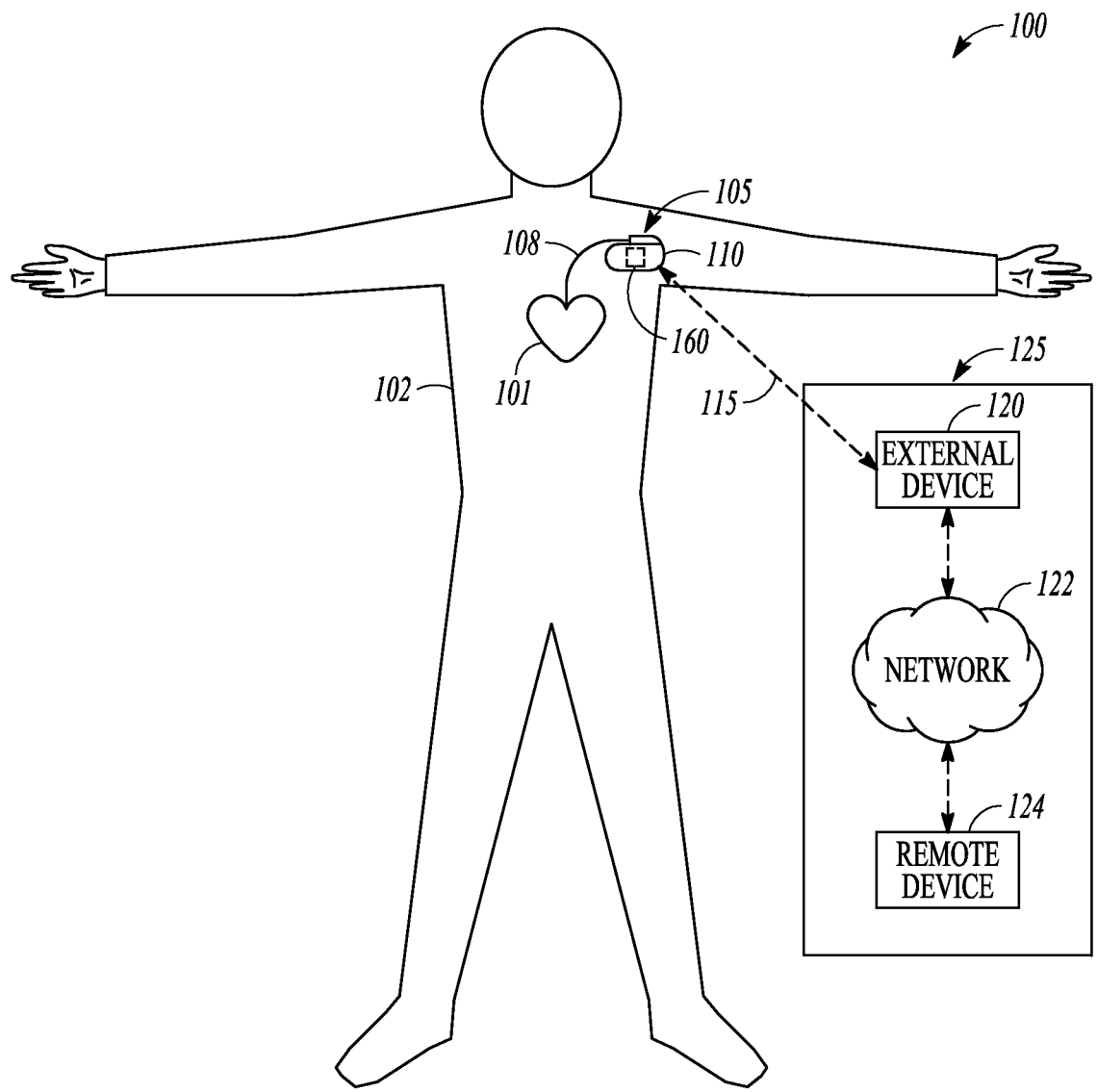
FIG. 1 illustrates generally an example of a patient management system and portions of an environment in which the system may operate.

Atrial tachyarrhythmia such as atrial fibrillation (AF) or atrial flutter (AFL) are characterized by fast atrial rate. In some patients, direct sensing of atrial activation rate with an electrode positioned in or near the atrium is not available or not feasible, such as patients not indicated for atrial lead implantation. A medical device, such as a single-chamber IMD with no dedicated atrial sensing/pacing lead, may detect an atrial tachyarrhythmia (AT) episode using ventricular heart rate, without direct sensing of atrial activity. However, confounding factors such as noise, motion artifacts, or cardiac rhythms other than the AT may be mistakenly detected as AT events. For example, during AFL, impulses from the atria are conducted to the ventricles through the atrio-ventricular node (AV node). Due primarily to its longer refractory period, the AV node may exert a protective effect on heart rate at the ventricle by blocking atrial impulses in excess of approximately 180 beats per minute (bpm). If an AFL rate is 300 bpm, a two-to-one (2:1) heart block may develop such that only half of the atrial impulses can be conducted to the ventricle, resulting in a ventricular rate of 150 bpm. As the heart rate is a measure of the ventricular rather than atrial activity, a medical device that detects AT using ventricular heart rate and not on atrial activity may be confounded by physiologic sinus rhythm at an elevated rate such as during tolerable physical activities (e.g., sinus tachycardia).

Arrhythmia can be detected using a comparison of a signal metric generated from a physiologic signal to a detection criterion, such as a detection threshold. An arrhythmia episode can be deemed sustained if the signal metric consistently satisfies the detection criterion for a specific period of time referred to as an arrhythmia duration. If the detection criterion is satisfied for a time period and then becomes unsatisfied before the arrhythmia duration is expired, then the arrhythmia episode is deemed non-sustained. Sustained and non-sustained arrhythmia episodes may have different etiologies and require different therapy regimens. Accordingly, accurate recognition of sustained or non-sustained arrhythmia episodes can be important in patient management.

Some arrhythmia episodes have corresponding signal metrics that satisfy the detection criterion, such as exceeding a detection threshold, with a wider margin. Detection of these episodes generally indicate a higher level of confidence of arrhythmia presence, such that the episodes are referred to as "definite episodes." In contrast, some other arrhythmia episodes have corresponding signal metrics that barely satisfy the detection criterion, such as exceeding the detection threshold with a narrower margin. Detection of these episodes generally indicate a lower level confidence of arrhythmia presence. As such, these episodes are referred to as "borderline episodes." Conventionally, the arrhythmia detection duration is typically programmed to a pre-determined value irrespective of the nature of the arrhythmia episodes experienced by the patient. For example, no distinction is made between the "definite episodes" and the "borderline episodes" when it comes to programming the arrhythmia detection duration. The pre-determined fixed detection duration may be less efficient, and can cause inappropriate detection of sustained arrhythmia episodes. For example, when a short detection duration is used, a borderline episode may be under-detected, or falsely detected as non-sustained arrhythmia due to intermittent satisfaction of the detection criterion. On the other hand, when a long detection duration is used, a positive detection decision of a sustained arrhythmia episode would not be made until the expiration of the long detection duration. For a definite episode, this may unnecessarily delay the detection of a sustained arrhythmia and proper and timely treatment or intervention. The longer detection duration also requires more computational resources and consumes more power.

For at least the foregoing reasons, the present inventors have recognized that the conventional pre-determined arrhythmia detection duration can decrease detection accuracy, result in lack of treatment or untimely treatment, or unnecessary or inappropriate therapies. False alerts to clinicians of the inappropriately detected arrhythmia, or presenting to clinicians a large volume of inappropriately detected arrhythmic events for review or adjudication, may adversely affect the device efficacy and unwarrantedly increase the healthcare cost associated with patient management. Consequently, this may diminish the clinical utility of the heart rate-based AT detection. Therefore, there is an unmet need for improved ambulatory arrhythmia detection system and methods that can automatically adjust the device settings for an individual patient to more accurately detect arrhythmia like atrial tachyarrhythmia.

Disclosed herein are systems, devices, and methods for detecting cardiac arrhythmia, such as an AT episode. An exemplary arrhythmia detection system can receive physiologic information of the patient, measure a first signal metric using a first portion of the received physiologic information, and determine an arrhythmia detection duration dynamically using a comparison between the measured first signal metric and a reference signal metric value. An arrhythmia detector can detect an AT episode using a second portion of the physiologic information corresponding to the determined arrhythmia detection duration.

The systems, devices, and methods discussed in this document, such as dynamic determination or adjustment of arrhythmia detection duration using arrhythmia characteristics, may improve the medical technology of automated cardiac rhythm management (CRM), and enhance the performance and functionality of an implantable medical device. In certain examples, the arrhythmia detection duration can be adjusted in accordance with a deviation of a signal metric, generated from patient physiologic information, from a reference signal metric value. Compared to conventional pre-determined detection duration irrespective of arrhythmia types (e.g., borderline episodes versus definite episodes), the dynamically adjusted detection duration can help improve AT detection sensitivity and specificity, particularly the borderline arrhythmia episodes with signal metrics barely satisfying the detection criterion. Patient care cost associated with false AT detections may therefore be reduced. Additionally, the dynamically adjusted detection duration can help avoid unnecessarily delay in detecting the definite arrhythmia episodes with signal metrics satisfying the detection criterion with wide margins, thus allowing for timely treatment or other clinician intervention. Moreover, such improvements in arrhythmia detection can be achieved with little to no additional cost or added system complexity. In some examples, existing system performance can be maintained (e.g., high arrhythmia detection sensitivity and specificity, etc.) using lower cost or less obtrusive systems, apparatus, and methods. With improved AT detection, fewer alarms are provided, battery life can be extended, fewer unnecessary drugs and procedures may be scheduled, prescribed, or provided, and an overall system cost and power savings may be realized in contrast to existing medical devices and systems.

FIG. 1 illustrates generally an example of a patient management system 100 and portions of an environment in which the system 100 may operate. The patient management system 100 may perform a range of activities, including remote patient monitoring and diagnosis of a disease condition. Such activities can be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiologic signal, such as using a physiologic sensor or the electrodes associated with the lead system 108. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature.

The AMD 110 may include a physiologic event detector circuit 160 configured to detect a physiologic event using the sensed physiologic signals. In an example, the physiologic event includes a cardiac arrhythmia episode, such as an episode of atrial fibrillation, atrial flutter, atrial tachycardia, supraventricular tachycardia, ventricular tachycardia, or ventricular fibrillation, cardiac pauses, among other brady- or tachy-arrhythmia. In an example, the physiologic event detector circuit 160 is configured to detect syncope, a presyncopal event or a precipitating event that may lead to a full-blown syncope. In some examples, the physiologic event detector circuit 160 is configured to detect worsening of a chronic medical condition, such as worsening heart failure (WHF). The physiologic event detector circuit 160 may execute a detection algorithm to monitor one or more physiologic signals continuously or periodically, and to detect the physiologic event automatically. Additionally or alternatively, the physiologic event detector circuit 160 may be configured to operate in a patient-triggered mode, register a patient-triggered episode and record physiologic data in response to a user-activated trigger. The trigger may be activated by the patient when the patient demonstrates certain signs or symptoms, or experiences a precursor event indicative of a medical event.

The AMD 110 may alternatively be configured as a therapeutic device configured to treat arrhythmia or other heart conditions. The AMD 110 may additionally include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmia, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmia or complications from arrhythmia.

The external system 125 may include a dedicated hardware/software system such as a programmer, a remote server-based patient management system, or alternatively a system defined predominantly by software running on a standard personal computer or a mobile device. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), analyzing the physiologic data to detect a cardiac arrhythmia, or optionally delivering or adjusting a therapy to the patient 102. Additionally, the external system 125 may receive device data from the AMD 110 via the communication link 115. Examples of the device data received by the external system 125 may include real-time or stored physiologic data from the patient 102, diagnostic data such as detection of cardiac arrhythmia or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of pad ent data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data, such as medical event episodes, may be collected by the AMD 110, among other data acquisition sensors or devices associated with the patient 102. The remote device 124 may include a storage unit to store the patient data in a patient database. The storage unit may additionally store an association between a plurality of episode characterizations and a plurality of detection algorithms for detecting a medical event having respective episode characterizations. The server may process the device-generated event episodes to verify that a specific medical event (e.g., a cardiac arrhythmia type) is detected such that the device-detected event is a true positive (TP) detection; or that no such medical event is detected such that the device-detected event is a false positive (FP) detection. The processing of the device-generated medical event episodes may be based on a stored association. In an example, a first event episode may be presented to a user (e.g., a clinician), who would provide an adjudication decision and a first episode characterization. If the adjudication decision indicates that the first event episode is a FP detection, then the server may identify from the stored association a detection algorithm corresponding to the first episode characterization, and process a second event episode using at least the identified detection algorithm to determine that the second event episode is either a TP or a FP detection. The server may schedule a presentation of at least a portion of the second episode using the processing result of the second episode. By using the detection algorithms tailored for recognizing episode with an episode characterization associated with a FP episode, more FP episodes having the same or similar episode characterization may be identified, and therefore avoided from being reviewed and adjudicated by the user. If the second event episode is determined to be a TP episode, then an alert is generated indicating further user review may be warranted.

By way of example, alert notifications may include a Web page update, phone or pager call, E-mail, SMS, text or "Instant" message, as well as a message to the patient and a simultaneous direct notification to emergency services and to the clinician. Other alert notifications are possible. In some examples, the server may include a medical event prioritizer circuit configured to prioritize the alert notifications. For example, an alert of a detected medical event may be prioritized using a similarity metric between the physiologic data associated with the detected medical event to physiologic data associated with the historical alerts.

The remote device 124 may additionally include one or more locally configured clients or remote clients securely connected over the network 122 to the server. Examples of the clients may include personal desktops, notebook computers, mobile devices, or other computing devices. Users, such as clinicians or other qualified medical specialists, may use the clients to securely access stored patient data assembled in the database in the server, and to select and prioritize patients and alerts for health care provisioning. The remote device 124, including the server and the interconnected clients, may execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected medical events to a user such as the patient or a clinician, or to a process including, for example, an instance of a computer program executable in a microprocessor. In an example, the process may include an automated generation of recommendations for a therapy, or a recommendation for further diagnostic test or treatment. In an example, the external device 120 or the remote device 124 may respectively include display units for displaying the physiologic or functional signals, or alerts, alarms, emergency calls, or other forms of warnings to signal the detection of arrhythmia. In some examples, the external system 125 may include an external data processor configured to analyze the physiologic or functional signals received by the AMD 110, and to confirm or reject the detection of the medical events. Computationally intensive algorithms, such as machine-learning algorithms, may be implemented in the external data processor to process the data retrospectively to detect cardia arrhythmia.

Portions of the AMID 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
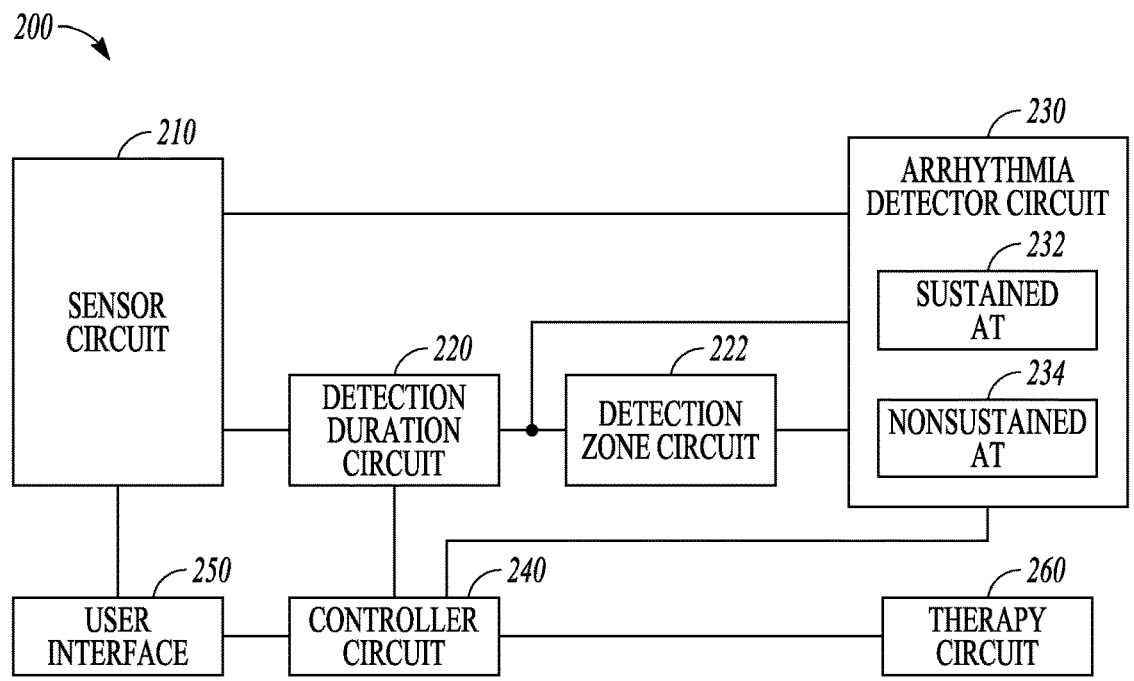
FIG. 2 illustrates generally an example of an arrhythmia detection system configured to detect an arrhythmia episode, such as an AT episode.

FIG. 2 illustrates generally an example of an arrhythmia detection system 200 configured to detect an arrhythmia episode, such as an AT episode. Portions of the arrhythmia detection 200 may be included in the physiologic event detector circuit 160 of the AMD 110. The arrhythmia detection system 200 may include one or more of a sensor circuit 210, a detection criterion circuit 220, an arrhythmia detector circuit 230, a controller circuit 240, and a user interface unit 250. The arrhythmia detection system 200 may additionally include an optional detection zone circuit 222 and an optional therapy circuit 260.

The sensor circuit 210 may include a sense amplifier circuit to sense a physiologic signal from a patient via one or more implantable, wearable, or otherwise ambulatory sensors or electrodes associated with the patient. The sensed physiologic signal may contain information about pulsatile cardiac activity, such as heart rate or pulse rate. Examples of the physiologic signals may include surface electrocardiography (ECG) such as sensed from electrodes on the body surface, subcutaneous ECG such as sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit 210 may include one or more other sub-circuits to digitize, filter, or perform other signal conditioning operations on the received physiologic signal.

In some examples, the physiologic signals may be stored in a storage device such as an electronic medical record system. The sensor circuit 210 may retrieve a physiologic signal from the storage device in response to a command signal that is provided by a system user, or automatically generated in response to occurrence of a specific event.

The detection criterion circuit 220 may be coupled to the sensor circuit 210 to measure a first signal metric (X) using a first portion of the received physiologic signal, compare the first signal metric (X) to one or more thresholds, and determine an AT detection criterion based on the comparison. In an example, if the first signal metric (X) is above a first threshold indicating a high confidence of presence of atrial tachyarrhythmia (AT), a first AT detection criterion can be generated. If the first signal metric (X) is below a second threshold lower than the first threshold which indicates a high confidence of absence of AT, a second AT detection criterion can be generated. If the signal metric (X) falls between the first and second thresholds indicating a relatively lower confidence about presence of absence of AT, then a third AT detection criterion can be generated. A second signal metric (Y) using a second portion of the received physiologic signal may then be used to detect AT using the corresponding arrhythmia detection duration.

In an example, the detection criterion circuit 220 may dynamically determine or adjust an arrhythmia detection duration using the first signal metric. Examples of the first signal metric (X) may include an atrial heart rate, ventricular heart rate, ventricular rate variability, or a cardiac signal morphology. In various examples, the first signal metric may include a statistical measure of ventricular rate or ventricular cycle length. One example of the statistical measure includes a ventricular rate pattern of consecutive decrease in ventricular rate. The ventricular rate pattern includes a pair of consecutive ventricular rate changes. Both ventricular rate changes are negative, referred to as a "double decrement" ventricular rate pattern. A double-decrement ratio, which represents a prevalence of the double decrement ventricular rate pattern over a specified time period or over a plurality of ventricular beats, may be computed, and used to detect AT (e.g., AF), or to distinguish AT from ectopic beats. The arrhythmia detector circuit 230 may determine a count of double-decrement beat pattern, or a double-decrement ratio. Such a baseline double-decrement pattern of ventricular rate may distinguish frequent premature ventricular contractions (PVCs) from an AT event, because PVCs alone typically do not produce double decrement patterns in ventricular rate. Krueger et al. U.S. patent application Ser. No. 14/825,669, entitled "ATRIAL FIBRILLATION DETECTION USING VENTRICULAR RATE VARIABILITY," refers to double decrement pattern in ventricular heart rate and its use in atrial arrhythmia detection, the disclosure of which is incorporated by reference herein in its entirety.

Another example of the statistical measure includes a ventricular rate cluster, represented by a statistical distribution or a histogram of ventricular rate or cycle length over multiple cardiac cycles. The ventricular rate cluster indicates regularity of ventricular rates of cardiac cycle lengths. Patients with AF are typically presented with irregular ventricular contractions. However, premature atrial contractions (PACs) may occur at irregular intervals. When PACs conduct to the ventricle, they may produce irregular ventricular rates, resulting in different ventricular clusters from AF. As such, the ventricular rate clusters may be used to distinguish frequent PACs from an AF event. Perschbacher et al. U.S. patent application Ser. No. 15/864,953 entitled "ATRIAL FIBRILLATION DISCRIMINATION USING HEART RATE CLUSTERING," refers to histogram clusters of ventricular rates and their use in discriminating between AF and non-AF events, the disclosure of which is incorporated by reference herein in its entirety.

Yet another example of the statistical measure includes a metric representing the occurrence of various beat patterns of the cycle lengths or heart rates. For example, the beat pattern may include a number or percentage of consecutive heart beats with each time period (e.g., a 2-minute time windows) that are within +/−5 bpm. In an example, the statistical measure includes an atrioventricular (AV) conduction block metric indicating a presence or degree of conduction abnormality during a sinus rhythm, such as a Wenckebach score representing the prevalence of Wenckebach block over a time period. Examples of the Wenckebach detector may be based on a repetitiveness indictor of various beat patterns of the cycle lengths or heart rates, such as discussed in Perschbacher et al. U.S. patent application Ser. No. 15/786,824 entitled "SYSTEMS AND METHODS FOR ARRHYTHMIA DETECTION," the disclosure of which is incorporated by reference herein in its entirety. Other examples of the statistical measure may include a signal morphology metric representing regularity of ventricular depolarization signal morphology during sinus rhythm, or a signal quality metric such as a signal-to-noise (SNR). The signal quality or signal morphology indicator may differentiate the AF from noise.

The detection criterion circuit 220 may determine an arrhythmia detection criterion, such as a detection duration (Dur), in accordance with a signal characteristic, such as the first signal metric (X), of the received physiologic signal. In an example, the arrhythmia detection duration (Dur) can be determined using a comparison of the first signal metric (X) to a reference signal metric value ($X_{REF}$). The $X_{REF}$ can be a user-programmable value. In an example, the arrhythmia detection duration (Dur) may be inversely proportional to a deviation of the measured first signal metric X from the reference $X_{REF}$. As such, a shorter detection duration can be used for detecting a sustained AT episode if the signal metric X exceeds the reference $X_{REF}$ by a wide margin, and a longer detection duration can be used for detecting a sustained AT episode if the signal metric X falls within a narrow margin of the reference $X_{REF}$. In an example, the arrhythmia detection duration (Dur) may be determined according to Equation (1) as follows:

$$Dur = w*1/|X-X_{REF}| \tag{1}$$

where w is a scaling factor. Examples of the detection duration (Dur) dynamically determined according to the deviation from $X_{REF}$ are discussed below, such as with reference to FIG. 3.

The arrhythmia detector circuit 230 may detect a cardiac arrhythmia using physiologic information, such as the physiologic signal received by the sensor circuit 210. By way of example, the cardiac arrhythmia may include atrial tachyarrhythmia, such as atrial fibrillation (AF), atrial flutter (AFL), atrial tachycardia, or paroxysmal supraventricular tachycardia (PSVT), among others. The arrhythmia detector circuit 230 may measure a second signal metric (Y) from a physiologic signal, and detect an AT episode using a comparison between the second signal metric and a specified detection criterion, such as a detection threshold. The arrhythmia detector circuit 230 may detect an AT episode using a second portion of the physiologic signal during the dynamically determined arrhythmia detection duration Dur, such as according to Equation (1) above. The second portion of the physiologic signal can be different from the first portion of the physiologic signal used by the detection criterion circuit 220 to determine or adjust the detection duration. In an example, the first portion can be a subset of the second portion of the physiologic signal, such that the first portion of the physiologic signal may also be used for detecting an AT episode.

Similar to the first signal metric, examples of the second signal metric (Y) may include an atrial heart rate, ventricular heart rate, ventricular rate variability, a cardiac signal morphology, or a statistical measure of ventricular rate or ventricular cycle length such as a ventricular rate cluster, a Wenckebach score, or a double-decrement ratio, as discussed above. In an example, the second signal metric (Y) may be the same type as the first signal metric (X). In another example, the second signal metric (Y) may be a different type as the first signal metric (X).

As illustrated in FIG. 2, the arrhythmia detector circuit 230 may be configured to identify an AT episode as a sustained AT episode 232 or a nonsustained AT episode 234. An AT episode is identified as sustained if the second portion of the physiologic information consistently satisfies a detection criterion (e.g., exceeding a threshold) through the determined arrhythmia detection duration. An AT episode is identified as nonsustained if the second portion of the physiologic information inconsistently satisfies the detection criterion during the determined arrhythmia detection duration. The arrhythmia detector circuit 230 may determine that no AT episode is present if the second portion of the physiologic information consistently fails to satisfy the detection criterion through the determined arrhythmia detection duration. In an example, the arrhythmia detector circuit 230 may evaluate the second signal metric (Y) over multiple time segments within the dynamically determined detection duration, and count those time segments with the corresponding signal metric exceeding a threshold $Y_{TH}$. In an example, the multiple time segments are two minutes long each and are consecutive in time. If the recognized time segments outnumbers a count threshold or a relative count threshold (e.g., 80% of all time segments evaluated), then the detection criterion is deemed to be consistently satisfied, and a sustained AT is detected. If the recognized time segments is below (or falls below) the count threshold or the relative count threshold, then the detection criterion is deemed to be inconsistently satisfied, and the AT episode is identified as nonsustainted.

In some examples, the system 200 may optionally include a detection zone circuit 222 configured to generate a plurality of distinct detection zones each defined by respective value ranges of the first signal metric X. The value ranges of different zones may be non-overlapping one another. By way of non-limiting example, the detection zone circuit 222 may determine a first zone Z(1) defined by an upper bound $X_{UB}(1)$ and a lower bound $X_{LB}(1)$, a second zone Z(2) defined by an upper bound $X_{UB}(2)$ and a lower bound $X_{LB}(2)$, etc. The upper and lower bounds of each zone may be determined with respect to the reference signal metric value $X_{REF}$, such as relative deviations from the $X_{REF}$. The detection criterion circuit 220 may determine, for the plurality of detection zones, respective zone-specific arrhythmia detection durations, such as a first duration Dur(1) for the first zone Z(1), a second duration Dur(2) for the second zone Z(2), etc. In an example, the zone-specific arrhythmia detection durations are inversely proportional to deviations of the respective value ranges (e.g., $X_{UB}$ or $X_{LB}$) from the reference signal metric value $X_{REF}$. To detect an AT episode, the arrhythmia detector circuit 230 may recognize, among the plurality of detection zones, a detection zone including the measured first signal metric X. For example, if $X_{LB}(k) < X < X_{UB}(k)$, then the AT detection can be performed in zone Z(k) defined by $X_{LB}(k)$ and $X_{UB}(k)$ through the zone-specific arrhythmia detection durations Dur(k) for the recognized zone Z(k). A sustained AT is detected in zone Z(k) if the second portion of the physiologic information consistently satisfies a detection criterion (e.g., a detection threshold) through the Dur(k). A nonsustained AT is detected in the detection zone Z(k) if the second portion of the physiologic information inconsistently satisfies the detection criterion through the Dur(k). Examples of the multi-zone AT detection with zone-specific arrhythmia detection durations are discussed below such as with reference to FIG. 4.

As illustrated in FIG. 2, the detection criterion circuit 220, the detection zone circuit 222, and the arrhythmia detector circuit 230 may respectively include circuit sets comprising one or more other circuits or sub-circuits. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

In various examples, one or more of the detection criterion circuit 220, the detection zone circuit 222, or the arrhythmia detector circuit 230 may be respectively implemented as a part of a microprocessor circuit. The microprocessor circuit may be a dedicated processor such as a digital signal processor, application specific integrated circuit (ASIC), microprocessor, or other type of processor for processing information including the physiologic signals received from the sensor circuit 210. Alternatively, the microprocessor circuit may be a general-purpose processor that may receive and execute a set of instructions of performing the functions, methods, or techniques described herein.

The controller circuit 240 controls the operations of the sensor circuit 210, the detection criterion circuit 220, the detection zone circuit 222, the arrhythmia detector circuit 230, and the user interface unit 250, and the data and instruction flow between these components. The user interface unit 250 may include an input device and an output device. In an example, at least a portion of the user interface unit 250 may be implemented in the external system 130. The input device may receive a user's programming input, such as parameters for adjusting detection criterion and parameters for detecting cardiac arrhythmia. The input device may include a keyboard, on-screen keyboard, mouse, trackball, touchpad, touch-screen, or other pointing or navigating devices. The input device may enable a system user to program the parameters used for sensing the physiologic signals, detecting the arrhythmias, and generating alerts, among others.

The output device may generate a human-perceptible presentation of the detected cardiac arrhythmia. The output device may include a display for displaying the sensed physiologic signal, intermediate measurements or computations such as dynamically determined detection duration, detection zones and zone-specific arrhythmia detection durations, and the detected sustained or nonsustained AT episodes, among others. The output unit may include a printer for printing hard copies of the detection information. The information may be presented in a table, a chart, a diagram, or any other types of textual, tabular, or graphical presentation formats. The presentation of the output information may include audio or other media format to alert the system user of the detected arrhythmic events. In an example, the output device may generate alerts, alarms, emergency calls, or other forms of warnings to signal the system user about the detected arrhythmic events.

The optional therapy circuit 260 may be configured to deliver a therapy to the patient in response to the detected cardiac arrhythmia. Examples of the therapy may include electrostimulation therapy delivered to the heart, a nerve tissue, other target tissues, a cardioversion therapy, a defibrillation therapy, or drug therapy. In some examples, the therapy circuit 260 may modify an existing therapy, such as adjust a stimulation parameter or drug dosage.

Figure 3:
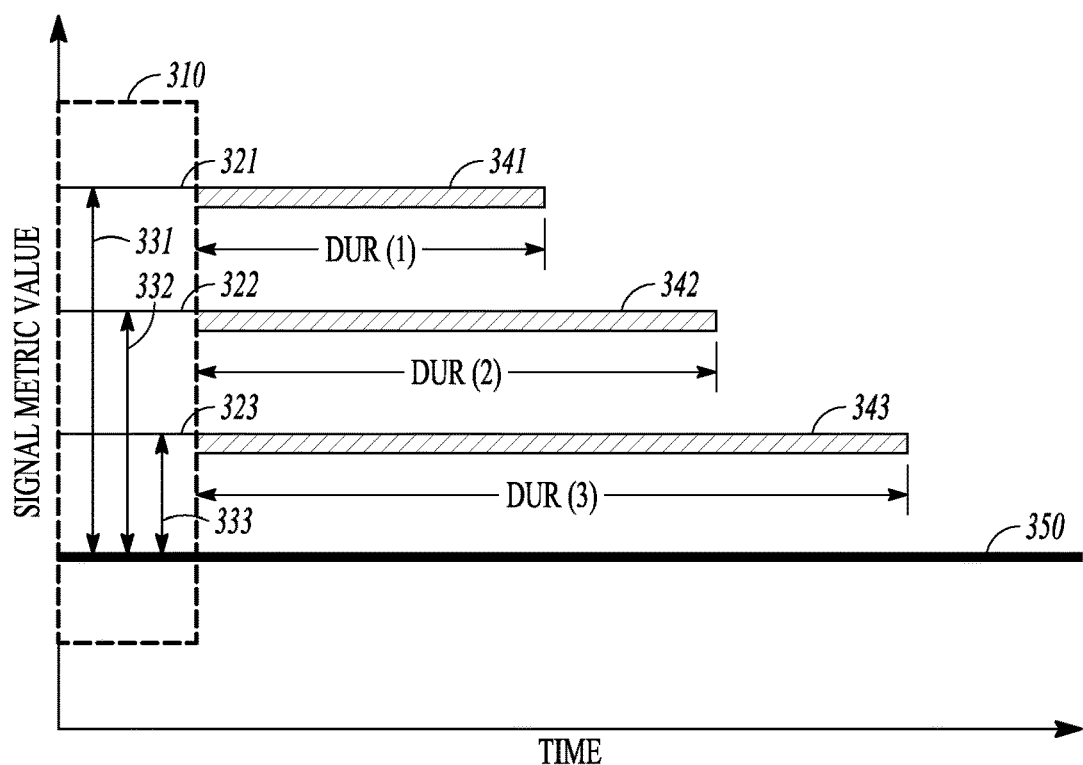
FIG. 3 is a diagram illustrating an example of dynamically determination of a detection duration using a signal metric generated from a physiologic signal.

FIG. 3 is a diagram illustrating an example of dynamic determination of a detection duration using a signal metric generated from a physiologic signal. By way of non-limiting example, FIG. 3 illustrates AT detection respectively performed on three physiologic signals, or three signal segments from a physiologic signal at different time. Examples of the physiologic signal may include cardiac electrical signals (e.g., ECG or intracardiac electrogram) or cardiac mechanical signals indicative of ventricular activation. A signal metric (X) may be generated respectively from the three physiologic signals, and monitored continuously or periodically during an initial detection window 310. If the signal metric (X) satisfies an initial detection criterion (e.g., exceeding an initial detection threshold), then the detection criterion circuit 220 can automatically determine a detection duration (Dur), such as using a deviation of the measured value of the signal metric (X) from a reference metric value ($X_{REF}$) 350. As illustrated in FIG. 3, during the initial detection window 310, the signal metric X(1) 321 of the first physiologic signal has the longest deviation 331 from the $X_{REF}$ 350, the signal metric X(2) 322 of the second physiologic signal has a shorter deviation 332, and the signal metric X(3) 323 of the third physiologic signal has the shortest deviation 333. Accordingly, the detection criterion circuit 220 can determine respectively a shortest detection duration Dur(1) 341 for the first physiologic signal, a longer detection duration Dur(2) 342 for the second physiologic signal, and a longest duration Dur(3) 343 for the third physiologic signal. A second signal metric (Y) may be generated from the respective physiologic signals. The arrhythmia detector circuit 230 may monitor the second signal metric Y during the dynamically determined detection durations, and detect a sustained or a nonsustained AT episode based on whether Y consistently satisfy a detection criterion through the corresponding detection durations, as discussed above with reference to FIG. 2.

Figure 4:
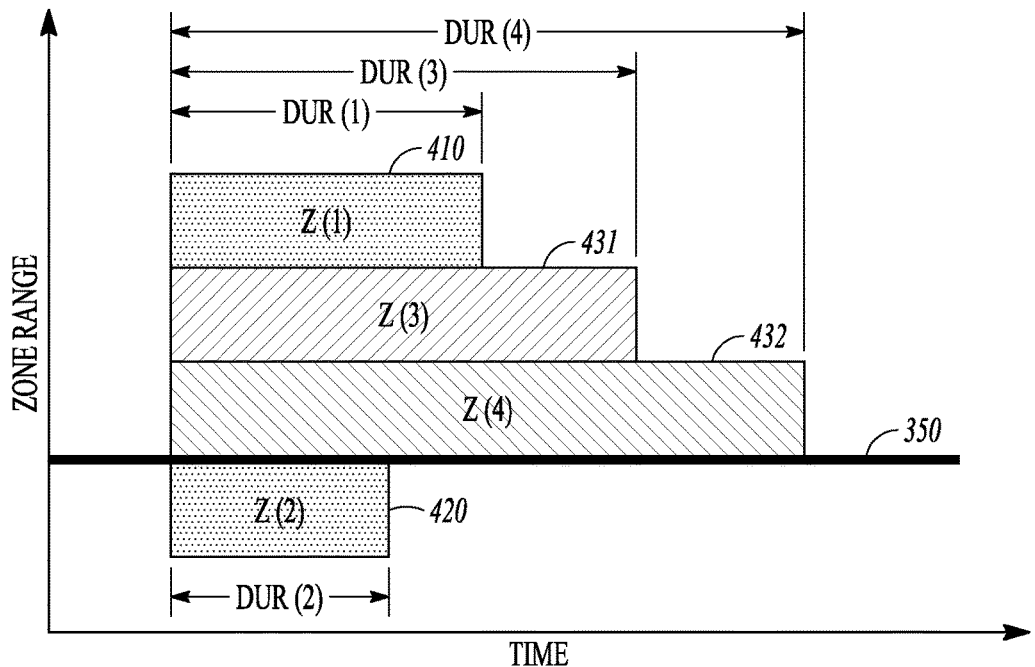
FIG. 4 is a diagram illustrating an example of multi-zone arrhythmia detection with dynamically determined zone-specific arrhythmia detection durations.

FIG. 4 is a diagram illustrating an example of multi-zone arrhythmia detection with dynamically determined zone-specific arrhythmia detection durations. The multiple detection zones, such as generated using the detection zone circuit 222, may be characterized by respective non-overlapping value ranges each defined by a lower bound ($X_{LB}$) and an upper bound ($X_{UB}$) of the first signal metric X. The $X_{LB}$ and $X_{UB}$ may be represented by deviations from a reference signal metric value $X_{REF}$. Associated with each zone includes a dynamically determined zone-specific arrhythmia detection duration, which can be inversely proportional to deviations of the value range (e.g., $X_{LB}$ and/or $X_{UB}$) of said zone from the reference metric value $X_{REF}$. Each zone may additionally have a corresponding AT detection criterion (e.g., a detection threshold for the second signal metric Y, as discussed above), which can be used by the arrhythmia detector circuit 230 to detect sustained or nonsustained AT episodes in the respective detection zones. In an example, the detection threshold in a detection zone is the lower bound $X_{LB}$ of the value range of that detection zone.

By way of non-limiting example and as illustrated in FIG. 4, the multiple zones may include a first detection zone Z(1) 410, a second detection zone Z(2) 420, and one or more intermediate detection zones, such as Z(3) 431 and Z(4) 432 that lie between zones Z(1) and Z(2). The first zone Z(1) 410 has a first value range, defined by $X_{LB}$ (1) and $X_{UB}$ (1), that exceeds the reference metric value $X_{REF}$ 350 by a first large margin. The detection zone Z(1) has a first zone-specific arrhythmia detection duration Dur(1), such as determined according to Equation (1). The arrhythmia detector circuit 230 may detect a sustained AT episode in zone Z(1) if the second signal metric Y consistently satisfies a detection criterion through the duration Dur(1). Because zone Z(1) is substantially high above the reference metric value $X_{REF}$ 350, events that satisfy the detection criterion in zone Z(1) are detected as, with a high level of confidence, sustained AT episodes. As such, the detection zone Z(1) can be used to detect sustained "definite episodes" with a high level of confidence of AT presence. A short Dur(1) for zone Z(1) is advantageous at least because it can help avoid unnecessarily delay in detecting the "definite episodes" of AT, thus allowing for timely treatment or clinician intervention.

The second detection zone Z(2) 420 is characterized by a second value range, defined by $X_{LB}$ (2) and $X_{UB}$ (2), below the reference signal metric value $X_{REF}$ 350 by a second margin. The detection zone Z(2) has a second zone-specific arrhythmia detection duration Dur(2), such as determined according to Equation (1). The detection zone Z(2) can be used to detect, or confirm, absence of an AT event. The arrhythmia detector circuit 230 may determine that no AT episode is present in zone Z(2) if the second signal metric Y consistently fails to satisfy the detection criterion through the duration Dur(2). The second duration Dur(2) can be equal to Dur(1). In an example, Dur(2) can be shorter than Dur(1). A shorter Dur(2) can help confirm absence of AT relatively quickly, and a longer Dur(1) can increase confidence of AT detection by reducing false-positive rate.

The one or more intermediate detection zones, such as Z(3) 431 and Z(4) 432, may each be characterized by a value range that lies between the first value range of zone Z(1) and the second value range of zone Z(2). Each intermediate detection zone has a corresponding zone-specific arrhythmia detection duration, such as Dur(3) for zone Z(3) and Dur(4) for zone Z(4), which can be determined according to Equation (1). Due to their closeness to the reference metric value $X_{REF}$, the durations Dur(3) and Dur(4) can be longer than the duration Dur(1) and Dur(2) in zones Z(1) and Z(2). The intermediate detection zones Z(3) and Z(4) can be used to detect the "borderline episodes". These borderline episodes generally have the second signal metric Y that intermittently satisfies the detection criterion during the detection duration, or exceeding the detection threshold with a narrower margin, which indicate generally a lower level confidence of AT presence. A relatively longer duration for an intermediate detection zone can help avoid or reduce chances of under-detection of AT episodes, or false identification of AT episodes as non-sustained due to intermittent satisfaction of the detection criterion in the respective intermediate detection zones. Accordingly, the zone-specific arrhythmia detection duration discussed herein can improve sensitivity and specificity of sustained AT detection, particularly the borderline arrhythmia episodes. In some examples, additional physiological information, such as cardiac or thoracic impedance, heart sounds, intracardiac acceleration, pressure, respiration, blood oxygen saturation, or physical activity or exertion level, may be used to augment the detection the "borderline episodes" in one or more intermediate detection zones, such as Z(3) 431 and Z(4) 432.

Figure 5:
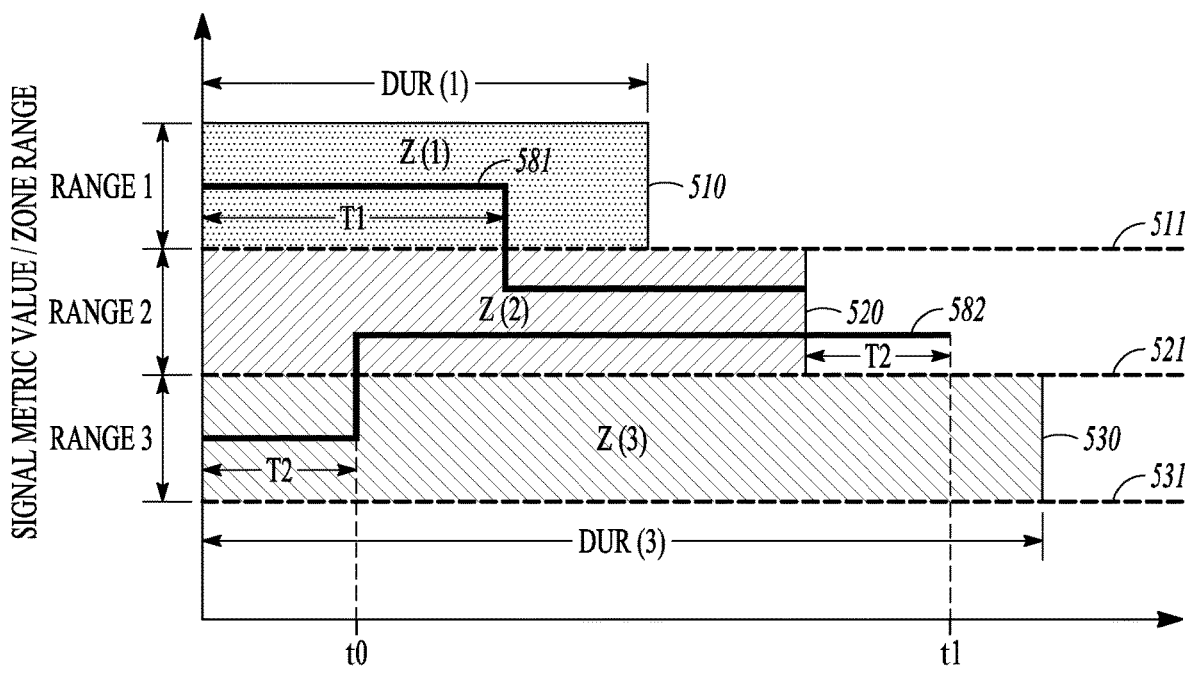
FIG. 5 is a diagram illustrating an example of a multi-zone AT detection in the event that a signal metric transition from one detection zone to another before expiration of a detection duration.

FIG. 5 is a diagram illustrating an example of a multi-zone AT detection in the event that signal metrics transition from one detection zone to another before expiration of a detection duration. By way of non-limiting example, three zones Z(1) 510, Z(2) 520, and Z(3) 530 are shown in FIG. 5, with respective zone ranges, zone-specific detection criterion (e.g., detection threshold), and zone-specific detection durations. In the example illustrated herein, the zone-specific detection thresholds, including threshold 511 for zone Z(1), threshold 521 for zone Z(2), and threshold 531 for zone Z(3), are chosen to be the lower bounds of the respective detection zones.

Upon initial detection, a proper detection zone is recognized to which an episode may belong, and a second signal metric Y can be monitored continuously or periodically through the duration of the recognized zone, as previously discussed with reference to FIG. 3. FIG. 5 illustrate a first episode 581 that transitions from a higher zone Z(1) to a lower zone Z(2), and a second episode 582 that transitions from a lower zone Z(3) to a higher zone Z(1). As the value ranges of the zones are non-overlapped to each other, if the second signal metric Y satisfies the detection criterion in a high zone (e.g., Z(1)), it would also satisfy the detection criterion in a lower zone (e.g., Z(2)). The episode 581 is initially in zone Z(1), and consistently exceeds the corresponding detection threshold 511 for a time duration of T1. Then, before reaching the end of duration Dur(1) of that zone, the second signal metric Y falls below the detection threshold 511, transitions to zone Z(2), and stays above the threshold 521 of zone Z(2) till the expiration of the duration Dur(2) in zone Z(2). Because the transition is from a higher zone to a lower zone, the time spent in Z(1), T1, is counted towards the time spent in the lower zone Z(2). As such, upon expiration of Dur(2), a sustained AT is detected in zone Z(2).

The episode 582 is initially in zone Z(3), and consistently exceeds the corresponding detection threshold 531 for a time duration of T2. Then, before reaching the end of duration Dur(3) of that zone, the second signal metric Y exceeds the detection threshold 521 of a higher zone Z(2) at time to, transitions to zone Z(2), and stays above the threshold 521 of zone Z(2) till the expiration of the duration Dur(2) in zone Z(2). Because the signal metric Y is below the threshold 521 of zone Z(2) during T2 (i.e., the time spent in zone Z(3) before zone transition occurs), T2 does not count towards the time spent in the higher zone Z(2). As such, the duration timer for zone Z(2) is reset at time to. A sustained AT is deemed detected in zone Z(2) at time t1 that extends beyond the expiration of Dur(2) of zone Z(2) with an additional interval T2.

Figure 6:
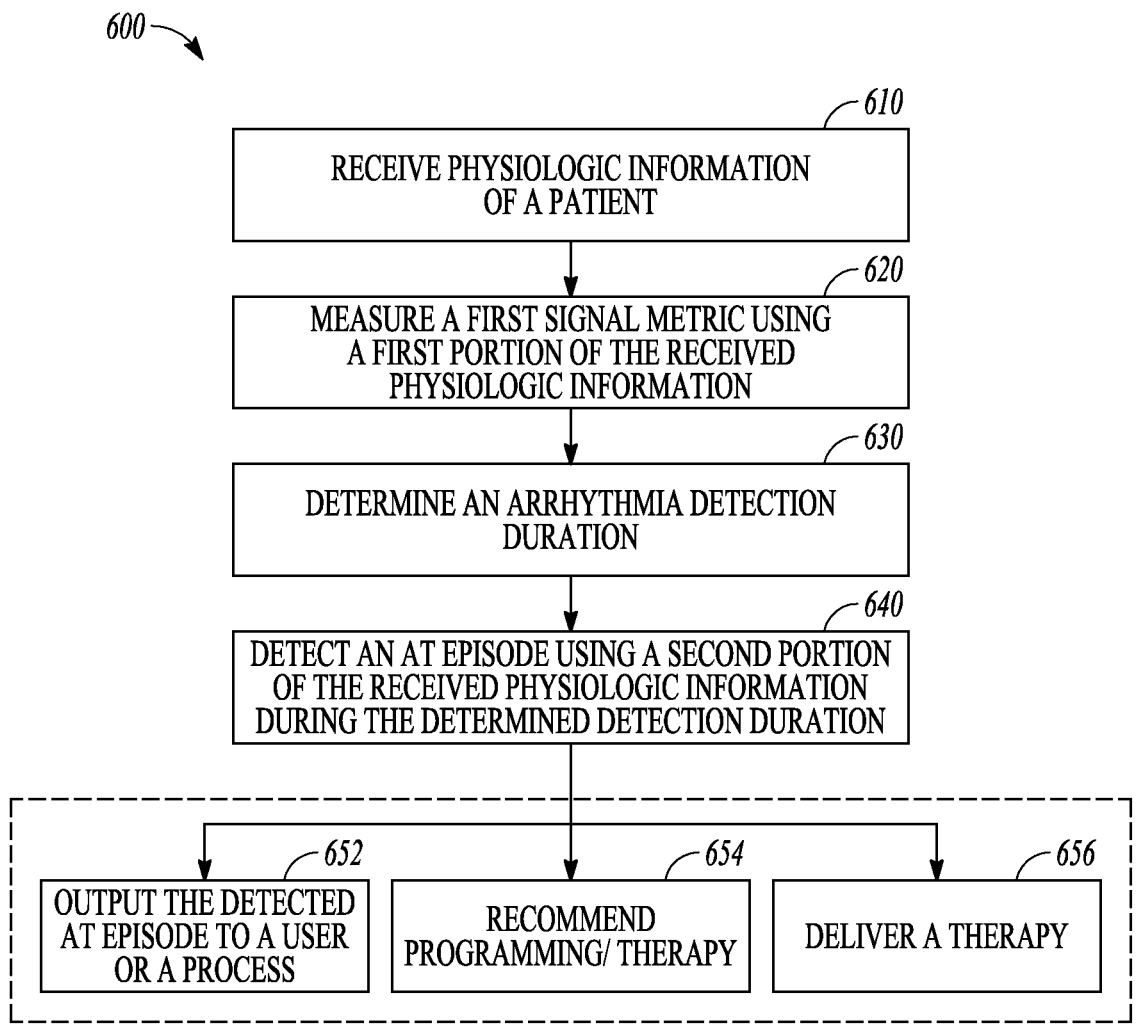
FIG. 6 is a flowchart illustrating an example of a method for detecting cardiac arrhythmia in a patient.

FIG. 6 is a flowchart illustrating an example of a method 600 for detecting cardiac arrhythmia in a patient, such as AT episode. Examples of atrial tachyarrhythmia that can be detected using the method 600 may include AF, AFL, atrial tachycardia, paroxysmal supraventricular tachycardia (PSVT), among others. The method 600 may be implemented and executed in an ambulatory medical device such as an implantable or wearable device, or in a remote patient management system. In an example, the method 600 may be implemented in and executed by the cardiac arrhythmia detection circuit 160 in the AMD 110, the external system 130, or the arrhythmia detection system 200.

The method 600 commences at step 610, where physiologic information of a patient may be received. The physiologic information may include physiologic signals sensed by one or more implantable, wearable, or otherwise ambulatory sensors. Examples of the physiologic signals may include cardiac electrical signals, such as ECG or EGM, or signals indicative of cardiac mechanical activity, such as pressure, impedance, heart sounds, or respiration signals. The sensed physiologic signal may be pre-processed, including amplification, digitization, filtering, or other signal conditioning operations. In some examples, patient physiologic signals may be sensed and stored in a storage device, such as an electronic medical record system, and retrieved for use such as according to the method 500.

At 620, a first signal metric can be measured from a first portion of a received physiologic signal, such as via the detection criterion circuit 220. Examples of the first signal metric may include an atrial heart rate, ventricular heart rate, ventricular rate variability, or a cardiac signal morphology. In various examples, the first signal metric may include statistical measure of ventricular rate or ventricular cycle length, such as a ventricular rate pattern, ventricular rate cluster, or Wenckebach score, as discussed above with reference to FIG. 2. At 630, an arrhythmia detection duration (Dur) may be determined using a comparison of the measured first signal metric to a reference signal metric value. In an example, the arrhythmia detection duration may be inversely proportional to a deviation of the measured first signal metric from the reference signal metric, such as according to Equation (1). A shorter detection duration may be used for detecting a sustained AT episode if the signal metric exceeds the reference metric by a wide margin, and a longer detection duration is used for detecting a sustained AT episode if the signal metric X is within a narrow margin of the reference metric.

In some examples, at 630, the arrhythmia detection duration may be respectively determined for two or more arrhythmia detection zones, such as the multiple detection zones as illustrated in FIG. 4. The distinct detection zones may each be defined by respective value ranges of the first signal metric, such as between an upper bound and a lower bound of the first signal metric. In an example, the value ranges of different zones are non-overlapping with each other. The upper and lower bounds of each zone may be determined using a deviation of the first signal metric relative to the reference signal metric. Zone-specific arrhythmia detection durations may be determined respectively for the detection zones. In an example, the zone-specific arrhythmia detection durations are inversely proportional to deviations of the respective value ranges from the reference signal metric. By way of non-limiting example, FIG. 4 illustrates a detection zone for detecting "definite arrhythmia episodes" with a high level of confidence of being a true sustained AT event. This zone is substantially high above the reference metric value, such that a relatively short detection duration is assigned thereto. Arrhythmic events detected therein have a high level of confidence of being sustained AT episodes. The short detection duration for this zone can help avoid unnecessarily delay in detecting those "definite episodes" of AT, thus allowing for timely treatment or clinician intervention. FIG. 4 also illustrates intermediate detection zones for detecting "borderline arrhythmia episodes" that have relatively a lower level confidence or presenting a sustained AT event. These intermediate zones are close to the reference metric value, such that a relatively longer detection is assigned thereto. A relatively longer duration for an intermediate detection zone can help avoid or reduce under-detection of a sustained AT event or falsely identifying the AT event as non-sustained due to intermittent satisfaction of the detection criterion in the immediate detection zone.

At 640, an AT episode may be detected using a second portion of the received physiologic information (e.g., a received physiologic signal) during the determined detection duration, such as using the arrhythmia detector circuit 230. The second portion of the physiologic signal can be different from the first portion of the physiologic signal used for determining or adjusting the detection duration. In an example, the first portion can be a subset of the second portion of the physiologic signal, such that the first portion of the physiologic signal is also used for detecting an AT episode. In an example, a second signal metric may be measured from a received physiologic signal. An episode can be detected using a comparison of the second signal metric against a specified detection criterion, such as a detection threshold. The second signal metric may include an atrial heart rate, ventricular heart rate, ventricular rate variability, a cardiac signal morphology, or a statistical measure of ventricular rate or ventricular cycle length such as a ventricular rate cluster, a Wenckebach score, or a double-decrement ratio, as discussed above. In an example, the second signal metric may be the same type as the first signal metric. In another example, the second signal metric may be a different type as the first signal metric.

The AT detection at 640 may include to identifying an AT episode as a sustained or a nonsustained AT episode. An AT episode is sustained if the second portion of the physiologic information consistently satisfies a detection criterion (e.g., exceeding a threshold) through the determined arrhythmia detection duration. An AT episode is nonsustained if the second portion of the physiologic information inconsistently satisfies the detection criterion during the determined arrhythmia detection duration. If the second portion of the physiologic information consistently fails to satisfy the detection criterion through the determined arrhythmia detection duration, then no AT episode is deemed detected at 640. In an example, the second signal metric may be measured over multiple time segments within the detection duration that has been determined at 630. The time segments with the corresponding second signal metric value exceeding a threshold can be recognized and counted. In an example, the multiple time segments are 2-minute long each and are consecutive in time. If the recognized time segments outnumbers a count threshold or a relative count threshold (e.g., 80% of all time segments evaluated), then an AT detection criterion is considered to be consistently satisfied; and a sustained AT is detected. If the recognized time segments is below (or falls below) the count threshold or the relative count threshold, then the detection criterion is considered to be inconsistently satisfied; and the AT episode is identified as nonsustainted.

In the event that multiple arrhythmia detection zones are generated and each assigned respective zone-specific arrhythmia detection durations, at 640, the AT detection may involve recognizing, among the plurality of detection zones, a detection zone containing the measured first signal metric, such as in an example as illustrated in FIG. 5. A sustained AT is detected in the recognized detection zone if the second signal metric consistently satisfies a detection criterion (e.g., a detection threshold) through the zone-specific arrhythmia detection duration for the recognized detection zone. A nonsustained AT is detected in the recognized detection zone if the second signal metric inconsistently satisfies the detection criterion through the zone-specific arrhythmia detection duration for the recognized detection zone.

The detected cardiac arrhythmia may be provided to one or more of the processes 652, 654, or 656. At 652, the detected AT episode may be output to a user or a process, such as via an output device of the user interface 250. In an example, the detected AT episode may be displayed on a display, including the sensed physiologic signal, intermediate measurements or computations such as dynamically determined detection duration, detection zones and zone-specific arrhythmia detection durations, and the detected sustained or nonsustained AT episodes, among others. Hard copies of the detection information may be generated. In various examples, alerts, alarms, emergency calls, or other forms of warnings may be generated to signal the system user about the detected arrhythmic episode.

At 654, a recommendation may be generated and provided to a user. The recommendation may include one or more of further diagnostic tests to be performed, anti-arrhythmic therapy to treat the detected arrhythmia or to alleviate the arrhythmic complications. The recommendation may include adjustment of one or more arrhythmia detection parameters, such as detection durations, upper and lower bounds of the detection zones, AT detection thresholds in the detection zones, among others. The method 600 may include the optional step 656 of delivering a therapy to the patient in response to the detected cardiac arrhythmia, such as via the optional therapy circuit 260 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified to treat the detected arrhythmia.

Figure 7:
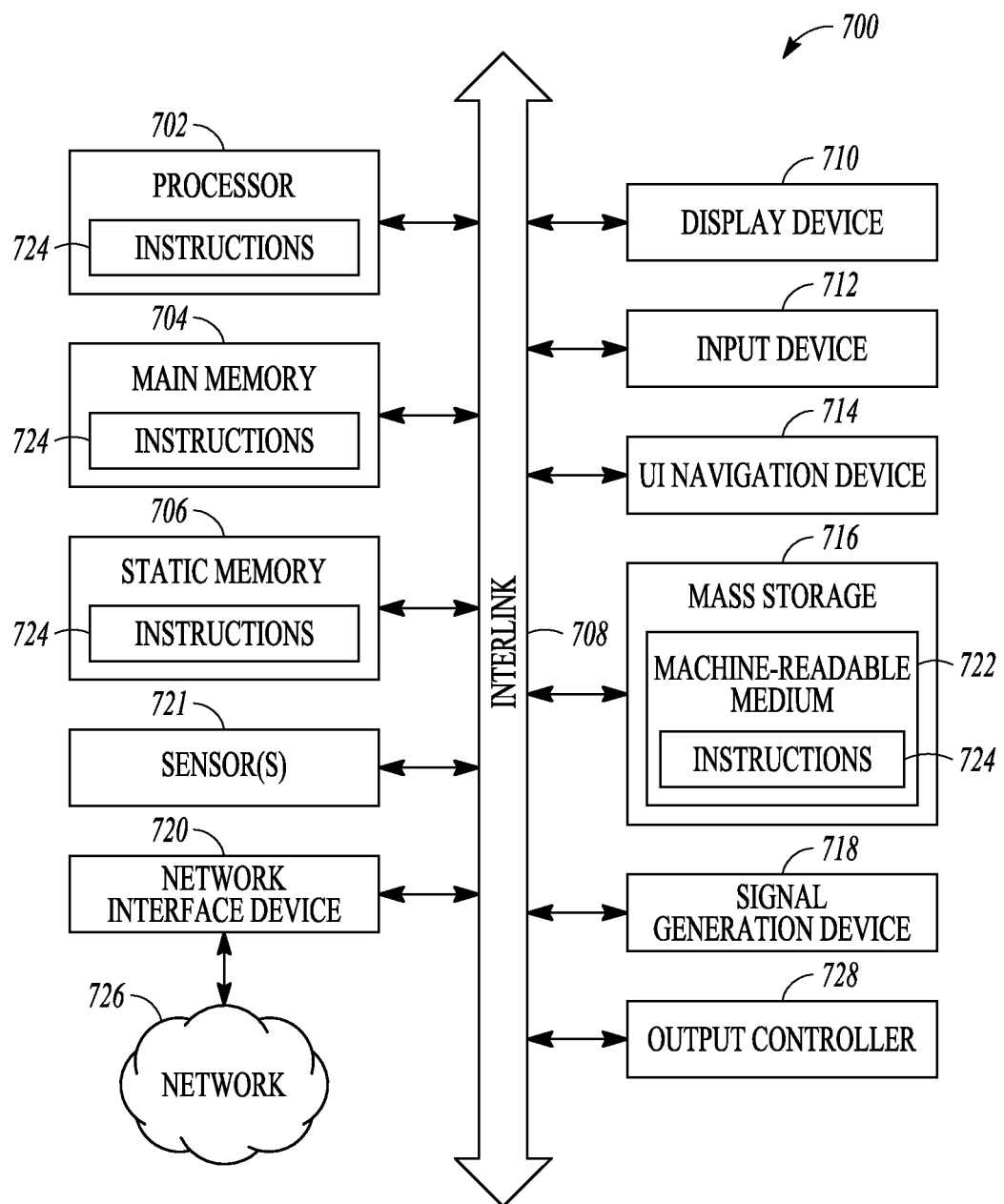
FIG. 7 illustrates generally a block diagram of an example machine upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the LCP device, the IMD, or the external programmer.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine-readable media.

While the machine-readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for optimizing ambulatory cardiac arrhythmia monitoring resources, comprising:
   an ambulatory medical device having a limited battery life for long-term patient monitoring over an extended period, the ambulatory medical device having different first and second arrhythmia detection durations, the first arrhythmia detection duration shorter than the second arrhythmia detection duration to optimize resources of the ambulatory medical device, including:
   a detection criterion circuit configured to:
      receive physiologic information of the patient;
      measure a first signal metric using a first portion of the received physiologic information;
      determine a confidence level of a presence of atrial tachyarrhythmia (AT) based on an amount of deviation of the measured first signal metric from at least one reference detection threshold; and
      transition between the first arrhythmia detection duration and the second arrhythmia detection duration based on the determined confidence level of the presence of AT, including to transition from the first arrhythmia detection duration to the second arrhythmia detection duration in response to a detected reduction in the determined confidence level of the presence of AT; and an arrhythmia detector circuit configured to detect an AT episode using a second portion of the received physiologic information in the second arrhythmia detection duration separate from and occurring subsequent to the first portion of the received physiologic information in the first arrhythmia detection duration.

2. The system of claim 1, wherein the arrhythmia detector circuit is configured to:
identify the AT episode as a sustained AT when the second portion of the physiologic information satisfies a detection criterion through the determined arrhythmia detection duration;
determine that no AT episode is present when the second portion of the physiologic information fails to satisfy the detection criterion through the determined arrhythmia detection duration; and
identify the AT episode as a non-sustained AT when the second portion of the physiologic information inconsistently satisfies the detection criterion during the determined arrhythmia detection duration.

3. The system of claim 2, wherein the detection criterion circuit is configured to determine the arrhythmia detection duration to be inversely proportional to the deviation of the measured first signal metric from the reference detection threshold.

4. The system of claim 2, comprising a detection zone circuit configured to generate a plurality of detection zones each characterized by respective non-overlapping value ranges of the first signal metric with respect to the reference detection threshold, and wherein:
the detection criterion circuit is configured to determine, for the plurality of detection zones, respective zone-specific arrhythmia detection durations; and
the arrhythmia detector circuit is configured to:
recognize, among the plurality of detection zones, a detection zone having a corresponding value range including the measured first signal metric; and
detect the sustained AT episode in the recognized detection zone using the second portion of the physiologic information during the zone-specific arrhythmia detection duration (ZDur) corresponding to the recognized detection zone.

5. The system of claim 4, wherein the zone-specific arrhythmia detection durations are inversely proportional to deviations of the respective value ranges of the plurality of detection zones from the reference detection threshold.

6. The system of claim 4, wherein the plurality of detection zones include:
a first detection zone characterized by a first value range of the first signal metric that exceeds the reference detection threshold by a first margin, the first detection zone having a first ZDur; and
a second detection zone characterized by a second value range of the first signal metric that is below the reference detection threshold by a second margin, the second detection zone having a second ZDur longer than the first ZDur.

7. The system of claim 6, wherein the arrhythmia detector circuit is configured to:
identify the AT episode as a sustained AT in the first detection zone when the second portion of the physiologic information satisfies a detection criterion through the first ZDur; and
determine that no AT episode is present in the second detection zone when the second portion of the physiologic information fails to satisfy the detection criterion through the second ZDur.

8. The system of claim 6, wherein the plurality of detection zones further include a third detection zone characterized by a third value range that lies between the first value range and the second value range, the third detection zone having a third ZDur longer than the first ZDur and the second ZDur.

9. The system of claim 4, wherein the arrhythmia detector circuit is configured to:
measure a second signal metric using the second portion of the received physiologic information;
identify the AT episode as a sustained AT in the recognized detection zone if the measured second signal metric exceeds a zone-specific detection threshold (ZTh) through the ZDur corresponding to the recognized detection zone; and
determine no AT episode is present in the recognized detection zone if the measured second signal metric is below the ZTh through the ZDur corresponding to the recognized detection zone.

10. The system of claim 9, wherein the ZTh is a lower bound of the value range of the recognized detection zone.

11. The system of claim 9, wherein the first and second signal metrics each include one of:
an atrial heart rate;
a ventricular heart rate variability;
a ventricular rate cluster;
a Wenckebach score;
a double-decrement ratio; and
a cardiac signal morphology.

12. The system of claim 1, wherein the ambulatory medical device further includes a therapy circuit configured to deliver a therapy to the patient in response to the detected AT episode.

13. The system of claim 1, wherein the detection criterion circuit is configured to dynamically determine a length of the second arrhythmia detection duration as a function of the first signal metric and a reference signal metric value.

14. A method for optimizing ambulatory cardiac arrhythmia monitoring resources, comprising:
receiving, via a detection criterion circuit of the ambulatory medical device, physiologic information of the patient;
measuring, via the detection criterion circuit, a first signal metric via a detection criterion circuit using a first portion of the received physiologic information;
determining a confidence level of a presence of atrial tachyarrhythmia (AT) based on an amount of deviation of the measured first signal metric from at least one reference detection threshold;
transitioning, via the detection criterion circuit, between a first arrhythmia detection duration and a second arrhythmia detection duration based on the determined confidence level of the presence of AT, the second arrhythmia detection criterion longer than the first arrhythmia detection duration to optimize resources of the ambulatory medical device, including transitioning from first arrhythmia detection duration to the second arrhythmia detection duration in response to detecting a reduction in the determined confidence level of the presence of AT; and
detecting an AT episode, via an arrhythmia detector circuit of the ambulatory medical device, using a second portion of the received physiologic information in the second arrhythmia detection duration separate from and occurring subsequent to the first portion of the received physiologic information in the first arrhythmia detection duration.

15. The method of claim 14, wherein detecting the AT episode includes:
   identifying the AT episode as a sustained AT when the second portion of the physiologic information satisfies a detection criterion through the determined arrhythmia detection duration;
   determining that no AT episode is present when the second portion of the physiologic information fails to satisfy the detection criterion through the determined arrhythmia detection duration; and
   identifying the AT episode as a non-sustained AT when the second portion of the physiologic information inconsistently satisfies the detection criterion during the determined arrhythmia detection duration.

16. The method of claim 14, wherein arrhythmia detection duration is determined to be inversely proportional to the deviation of the measured first signal metric from the reference detection threshold.

17. The method of claim 14, comprising:
   generating a plurality of detection zones each characterized by respective non-overlapping value ranges of the first signal metric with respect to the reference detection threshold;
   determining, for the plurality of detection zones, respective zone-specific arrhythmia detection durations; and
   recognizing, among the plurality of detection zones, a detection zone having a corresponding value range including the measured first signal metric; and
   wherein detecting an AT episode includes detecting a sustained AT episode in the recognized detection zone using the second portion of the physiologic information during the zone-specific arrhythmia detection duration (ZDur) corresponding to the recognized detection zone.

18. The method of claim 17, wherein the plurality of detection zones include:
   a first detection zone characterized by a first value range of the first signal metric that exceeds the reference detection threshold by a first margin, the first detection zone having a first Zdur;
   a second detection zone characterized by a second value range of the first signal metric that is below the reference detection threshold by a second margin, the second detection zone having a second ZDur; and
   a third detection zone characterized by a third value range that lies between the first value range and the second value range, the third detection zone having a third ZDur longer than the first ZDur and the second ZDur.

19. The method of claim 17, comprising measuring a second signal metric using the second portion of the received physiologic information, and wherein detecting a sustained AT episode includes:
   identifying the AT episode as a sustained AT in the recognized detection zone when the measured second signal metric exceeds a zone-specific detection threshold (ZTh) through the ZDur corresponding to the recognized detection zone; and
   determining that no AT episode is present in the recognized detection zone when the measured second signal metric is below the ZTh through the ZDur corresponding to the recognized detection zone.

20. The method of claim 14, comprising dynamically determining, via the detection criterion circuit, a length of the second arrhythmia detection duration as a function of the first signal metric and a reference signal metric value.

* * * * *